(12) United States Patent
Schanzer et al.

(10) Patent No.: US 10,712,240 B2
(45) Date of Patent: Jul. 14, 2020

(54) CONTAMINANT MONITOR SYSTEM AND METHOD

(71) Applicants: Ariana Schanzer, Englewood, NJ (US);
Michale Goldberger, Skokie, IL (US);
Aardra Rajendran, Lewisville, NC
(US); Adam Weisel, Teaneck, NJ (US)

(72) Inventors: Ariana Schanzer, Englewood, NJ (US);
Michale Goldberger, Skokie, IL (US);
Aardra Rajendran, Lewisville, NC
(US); Adam Weisel, Teaneck, NJ (US)

(73) Assignee: Ariana Schanzer, Englewood, NJ (US)

( * ) Notice: Subject to any disclaimer, the term of this patent is extended or adjusted under 35 U.S.C. 154(b) by 432 days.

(21) Appl. No.: 15/491,918

(22) Filed: Apr. 19, 2017

(65) Prior Publication Data

US 2017/0299502 A1    Oct. 19, 2017

Related U.S. Application Data

(60) Provisional application No. 62/324,863, filed on Apr. 19, 2016.

(51) Int. Cl.
*G01N 1/20* (2006.01)
*G01N 21/77* (2006.01)
(Continued)

(52) U.S. Cl.
CPC .......... *G01N 1/2035* (2013.01); *G01N 21/77* (2013.01); *G01N 21/8483* (2013.01);
(Continued)

(58) Field of Classification Search
CPC .. G01N 1/2035; G01N 21/77; G01N 33/1813; G01N 21/94; G01N 21/8483;
(Continued)

(56) References Cited

U.S. PATENT DOCUMENTS

| 2,105,226 A | 1/1938 | Pratt |
| 4,663,358 A | 5/1987 | Hyon et al. |

(Continued)

FOREIGN PATENT DOCUMENTS

| CN | 204694629 U | 10/2015 |
| CN | 106198416 A | 12/2016 |

(Continued)

OTHER PUBLICATIONS

Hach Company (2017) "Product—Pocket Colorimeter™ II," Accessible on the Internet at URL: https://www.hach.com/pockets. [Last Accessed Jul. 18, 2017].

(Continued)

*Primary Examiner* — Samuel P Siefke
(74) *Attorney, Agent, or Firm* — Lathrop GPM LLP

(57) ABSTRACT

Embodiments of the present invention are directed to methods, systems, and software for assessing contaminant quantities in a fluid. Fluid enters a reaction chamber. A controller then signals two different sheets with different reagents to move into the reaction chamber. One sheet contains reagents to form a contaminant byproduct or gas, while the other sheet is saturated with reagent that will have a photometric effect upon reacting with the contaminant byproduct or gas. After the photometric effect has occurred, the controller moves the reacted portion of the other reagent sheet into alignment with a photometric sensor. This photometric effect is calculated to contaminant concentration. The concentration is recorded and the data is transmitted to memory. The fluid sample in the chamber is drained and the remaining solid waste is collected onto the first reagent sheet. Both sheets are individually collected into separate controllable collectors.

17 Claims, 11 Drawing Sheets

(51) Int. Cl.
*G01N 33/18* (2006.01)
*G01N 21/94* (2006.01)
*G01N 21/84* (2006.01)
*G01N 21/78* (2006.01)

(52) U.S. Cl.
CPC .......... *G01N 21/94* (2013.01); *G01N 33/1813* (2013.01); *G01N 21/78* (2013.01); *G01N 2001/205* (2013.01); *G01N 2021/7759* (2013.01); *G01N 2021/7773* (2013.01); *G01N 2021/7786* (2013.01)

(58) Field of Classification Search
CPC ........... G01N 21/78; G01N 2021/7759; G01N 2021/7786; G01N 2021/7773; G01N 2001/205
IPC ..................................................... G01N 1/2085
See application file for complete search history.

(56) References Cited

U.S. PATENT DOCUMENTS

| | | | |
|---|---|---|---|
| 4,797,000 A | | 1/1989 | Curtis |
| 5,004,582 A | * | 4/1991 | Miyata ...................... B01L 7/00 422/404 |
| 5,116,759 A | | 5/1992 | Klainer et al. |
| 5,330,917 A | | 7/1994 | Stone |
| 5,408,535 A | * | 4/1995 | Howard, III ....... G01N 21/8483 382/128 |
| 5,643,351 A | | 7/1997 | Lew et al. |
| 6,284,546 B1 | * | 9/2001 | Bryning ................ B01F 5/0085 250/458.1 |
| 6,696,300 B1 | | 2/2004 | Jaunakais et al. |
| 6,753,186 B2 | | 6/2004 | Moskoff |
| 7,336,362 B2 | | 2/2008 | Van Geen |
| 7,424,399 B2 | | 9/2008 | Kahn et al. |
| 8,666,431 B2 | | 3/2014 | Kim et al. |
| 9,057,705 B2 | | 6/2015 | Yang et al. |
| 2003/0030800 A1 | | 2/2003 | Golden et al. |
| 2006/0007445 A1 | | 1/2006 | Van Geen |
| 2009/0097020 A1 | * | 4/2009 | Treado ................... G01N 21/64 356/301 |
| 2009/0111191 A1 | * | 4/2009 | Bonne ................ G01N 21/8483 436/164 |
| 2010/0332149 A1 | | 12/2010 | Schlopp |
| 2012/0304729 A1 | * | 12/2012 | O'Dell ................. G01N 21/783 73/1.02 |

FOREIGN PATENT DOCUMENTS

| | | |
|---|---|---|
| EP | 0 842 657 A1 | 5/1998 |
| GB | 2423582 A | 8/2006 |
| JP | 2003-066025 A | 3/2003 |
| JP | 2015-102380 A | 6/2015 |
| WO | 1998/000170 A1 | 1/1998 |
| WO | 2005/087201 A1 | 9/2005 |
| WO | 2010/079466 A2 | 7/2010 |
| WO | 2012/003367 A2 | 1/2012 |
| WO | 2015/177792 A1 | 11/2015 |

OTHER PUBLICATIONS

Nagy et al. (Sep. 2016) "The Effect of Elevated Water Sample Temperature on the Performance of a Custom-developed Colorimetric Arsenic Sensor," Procedia Engineering. 168:1479-1482.

* cited by examiner

CONTAMINANT MONITOR SYSTEM AND METHOD

CROSS REFERENCE TO RELATED APPLICATIONS

This application claims priority to U.S. Provisional Patent Application Ser. No. 62/324,863, filed Apr. 19, 2016, the disclosure of which is incorporated herein by reference in its entirety.

FIELD

Embodiments of the present disclosure are directed to methods and apparatus for assessing and quantifying contaminates in a fluid.

BACKGROUND

Access to clean water can often evade even those in the developed world. More than 783 million people around the world suffer because of contamination of their water supply. For example, arsenic is a toxic substance due to its threat to human health and the high likelihood of being exposed. Over 140 million people have arsenic contamination in their water supplies. Prolonged arsenic poisoning has been linked to various cancers, reproductive disorders, dermatological problems and more. Technological advances can play a vital role in addressing this and other water contamination issues.

By detecting contaminants at 'point of source', toxic exposures can be avoided and sources of contamination can be identified and mitigated in a timelier manner. Thus, there is a need for enhancing field test methods as well as creating automatic 'on the tap' monitors for consistent, rapid, and affordable data collection of contaminants in drinking water.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

Contaminants to drinking water or ground water may be any of the following categories: physical, chemical, biological, and radiological. Physical contaminants are sediment or organic material. Chemical contaminants may be, for example, nitrogen, metals, toxins produced by bacteria, human or animal pharmaceuticals, pesticides, bleach and salts. Biological contaminants are organisms such as bacteria, viruses, protozoan, and parasites. Radiological contaminants are chemical in nature with unstable atoms that emit ionizing radiation, such as cesium, plutonium, and uranium.

With this novel method of reagent delivery, the user does not need to replace the reagents within the device for months at a time. This system is uniquely engineered to be easy to use, accurate, efficient, effective, and a long term solution to contaminant monitoring and quantifying.

In one embodiment, a contaminant sensor system includes: a reaction chamber having a cavity; a valve connected to the reaction chamber, the valve allowing a fluid into the reaction chamber cavity; a first reagent sheet having a length such that the first reagent sheet enters the cavity of the reaction chamber at a first aperture and passes through and out of the cavity of the reaction chamber at a second aperture, the first reagent sheet including at least one first reagent on the first reagent sheet, wherein the at least one first reagent reacts with the fluid in the reaction chamber; a first controllable loader loading an unused portion of the first reagent sheet into the reaction chamber; a first controllable collector collecting a used portion of the first reagent sheet; and a first photometric detector capable of detecting a photometric property.

In another embodiment, the contaminant sensor system further includes a second reagent sheet having at least one second reagent capable of changing a detectable photometric property when reacting with at least one of a contaminant and a contaminant byproduct, the at least one second reagent being embedded into the second reagent sheet and the second reagent sheet being located above the first and second apertures; a second controllable loader loading an unused portion of the second reagent sheet into the reaction chamber; a second controllable collector collecting a used portion of the second reagent sheet; and a second photometric detector capable of detecting a photometric property. Optionally, a first photometric detector is not included; only a second photometric detector is included.

In a method of sensing a contaminant in a fluid includes the steps of: the fluid entering a cavity of a reaction chamber; operating at least one motor to control at least one of a controllable loader and a controllable collector such that an unused portion of a first reagent sheet having a first reagent is moved within the reaction chamber; at least one reagent reacting with a contaminant in the fluid to create at least one of a contaminant and a contaminant byproduct; the at least one of contaminant and contaminant byproduct reacting with a portion of the first reagent sheet to produce a change in the photometric property of the first reagent sheet; operating at least one motor to control at least one of a controllable loader and a controllable collector such that a used portion of a first reagent is moved to align with a photometric sensor capable of detecting a change in a photometric effect; correlating the change in the photometric property in the first reagent sheet with a contaminant concentration in the fluid.

In another method of sensing a contaminant in a fluid includes the steps of: the fluid entering a cavity of a reaction chamber; operating at least one motor to control at least one of a first controllable loader and a first controllable collector such that an unused portion of a first reagent sheet having a first reagent is moved within the reaction chamber; at least one reagent reacting with a contaminant in the fluid to create a contaminant byproduct; operating at least one motor to control at least one of a second controllable loader and a second controllable collector such that an unused portion of a second reagent sheet having a second reagent is moved above the first reagent sheet; the contaminant byproduct reacting with a portion of the second reagent sheet to produce a change in a photometric property of the second reagent sheet; operating at least one motor to control at least one of a second controllable loader and a second controllable collector, such that the changed portion of the second reagent sheet is aligned with a photometric detector; and correlating the change in the photometric property in the second reagent sheet with a contaminant concentration in the fluid.

Novel and unobvious contaminant sensor systems and methods are set forth herein, as will be evident from reviewing the description below and the accompanying drawings.

BRIEF DESCRIPTION OF THE DRAWINGS

The drawings constitute a part of this specification and may include exemplary embodiments of the present disclosure and illustrate various objects and features thereof.

A further understanding of the disclosure may be had by reference to the accompanying drawing in which.

DETAILED DESCRIPTION

Embodiments will now be described in detail with respect to an apparatus and method for assessing contaminants in fluids. As used herein, fluid refers to gas or liquid. The details reflect the inventors' present preferred embodiments and the best means for practicing the invention. Those skilled in the art will recognize that the embodiments described herein are subject to modification and alteration without departing from the teaching herein. Therefore, the present discussion should not be considered limiting but an exemplification of the features of the invention.

Figure 1:
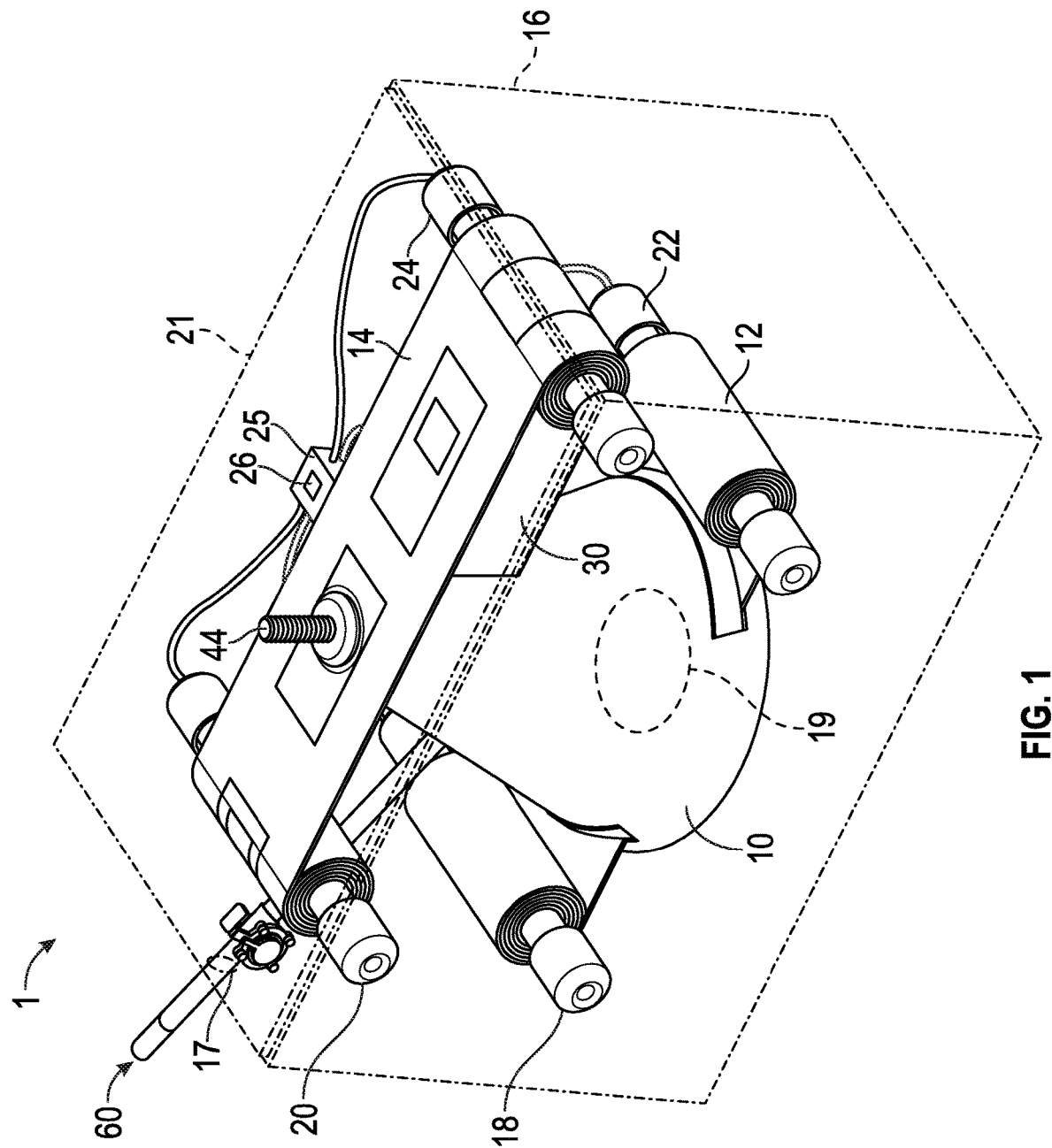
FIG. 1 is a perspective view of a contaminant sensor system according to an embodiment with the housing shown in phantom.
Figure 2:
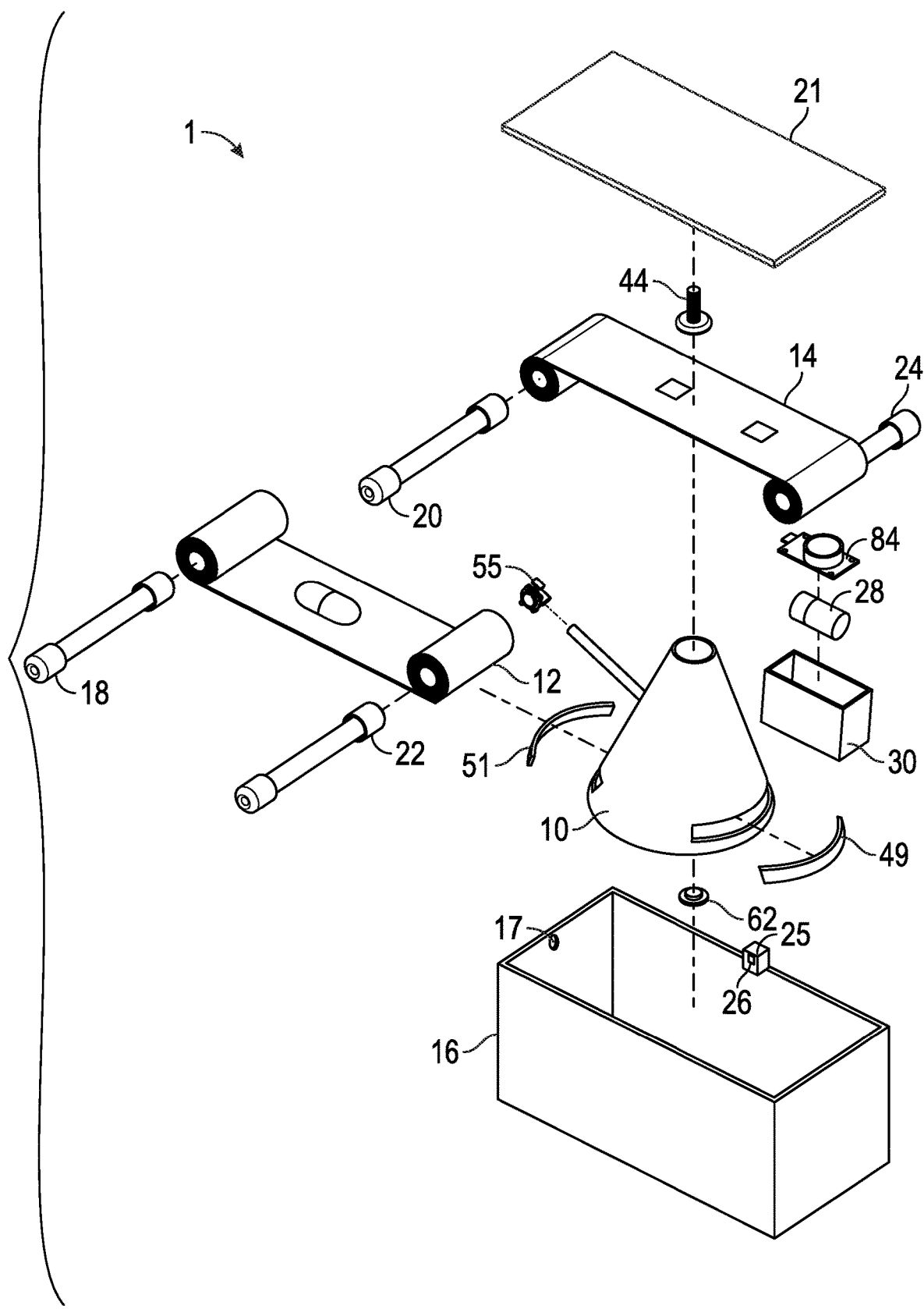
FIG. 2 is an exploded view of a contaminant sensor system according to an embodiment.

Turning now to FIGS. 1 and 2, a contaminant sensor system, generally designated by the numeral 1, embodying features of the present disclosure is depicted. The system 1 can be used in the home, in the field or in commercial settings. The system 1 includes a reaction chamber 10, a first reagent sheet or belt 12, a second reagent sheet or belt 14, an outer housing 16, a first controllable loader 18, a second controllable loader 20, a first controllable collector 22, a second controllable collector 24, at least one motor 25, a controller 26, a power source 28, and a photometer assembly 30. The first reagent sheet 12 is situated through the reaction chamber 10 and the second reagent sheet 14 is located above the first reagent sheet. The reaction chamber 10, the first reagent sheet 12, the second reagent sheet 14, the first controllable loader 18, the second controllable loader 20, the first controllable collector 22, the second controllable collector 24, the controller 26, the power source 28, and the photometer assembly 30 may be all situated within the outer housing 16. The outer housing 16 includes a fluid inlet aperture 17, a fluid outlet aperture 19, and a removable top 21. The housing acts as an extra barrier between users and the chemical reactions and byproduct(s) of those reactions. The first controllable loader 18, the second controllable loader 20, the first controllable collector 22, and the second controllable collector 24 may be removeably connected to the outer housing 16.

Figure 3A:
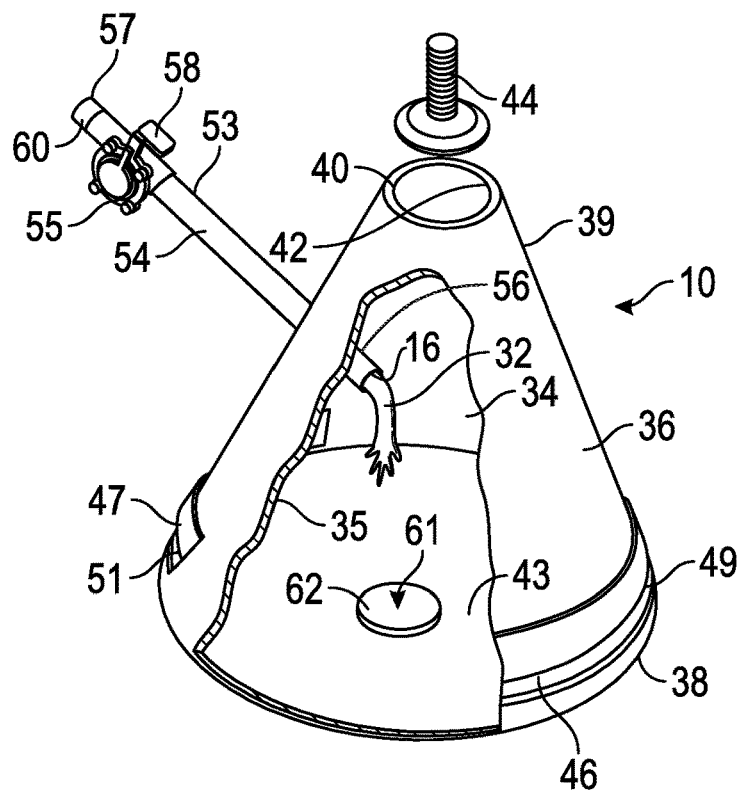
FIG. 3A is a perspective view of the reaction chamber and a fluid entry valve.

Referring now to FIG. 3A, the reaction chamber 10 is the compartment of the system 1 where a fluid sample 32 is chemically tested. The reaction chamber 10 is illustrated as frusto-conical in shape, and includes a hollow cavity or chamber 34 defining an inner surface 35. It is foreseen that the reaction chamber 10 may be any geometric shape, i.e. frusto-pyramidal, circular, square, rectangular, trapezium, hexagonal, frusto-biconical etc. It is foreseen that an upper portion 39 of the reaction chamber 10 funnel or taper inward, as this allows gases formed during chemical reactions to concentrate at the upper portion 39 of the reaction chamber 10. The reaction chamber 10 may be made from a gas impermeable material, such as high density poly(ethylene) HPDE (0.964 g/cm$^3$), which has an oxygen permeability coefficient of 0.3, 25° C. (P×10$^{10}$), or Poly(vinyl chloride) PVC, which has an oxygen permeability coefficient of 0.045, 25° C. (P×10$^{10}$), or a glass like borosilicate glass (e.g. Pyrex) which is durable, dense, has a low coefficient of expansion and a low permeability to reactive gas. These low permeability constants ensure that a reactive gas will not escape the chamber 10.

The reaction chamber 10 has an outer surface 36, a bottom surface 38, and a top surface 40. The top surface 40 has a top aperture 42 that is closed or sealed off by a stopper 44. The stopper 44 acts like a plug to seal the cavity 34 to capture the reacting components within as will be further discussed below. The stopper 44 is circularly shaped to cover the circular aperture 42, but both the stopper 44 and the aperture may be any geometric shape, and the illustrated example is not meant to be limiting. The stopper 44 is electronically connect with the controller 26, as will be further discussed below. The outer surface has two opposed apertures 46, 47 near the bottom surface 38. Each aperture 46, 47 may be identical to each other and are sized and shaped to allow the first reagent sheet 12 therethrough. The opposed apertures 46, 47 are near enough to the bottom surface 38 such that when the fluid is drained from the reaction chamber 10, the first reagent sheet 12 maximizes capture of solid waste. Each of the apertures 46, 47 may be substantially sealed by airtight chamber doors 49, 51 or other such means, for example, a rubber sealant. The doors 49, 51 may be electronically connected to the controller 26. The doors 49, 51 may have a portion that engages the first reagent sheet 12 to hold the sheet in position near a bottom surface 43 of the inner surface 35.

The inner surface 35 may include a coating, fabric, or at least one layer of a nonporous, hydrophobic, long lasting, low coefficient of friction, low permeability, non-reactive material, to prevent residue build up inside of the reaction chamber 10. Many such examples of such a material exist, such as a polytetrafluoroethylene (Teflon), polyteflon (porous or nonporous), graphene or graphene based materials (graphene oxide), carbon nano-tube, silica-based coatings/ silica nano-coatings, precipitated calcium carbonate, zinc-oxide polystyrene, zinc-oxide polystyrene nano-composite, manganese oxide polystyrene, manganese oxide polystyrene nano-composite, lanthanide ceramics, titanium dioxide materials and compounds, polystyrene materials and compounds, nano-sharp glass cone surface, borosilicate, Never-Wet, UltraDry, Water Beader, Nanomyte, diatomaceous earth, Paints: such as Latex or Acrylic Latex, one part epoxy, oil based enamel, cobalt hydroxide film, polyallylamine hydrochloride (PAH), fluorinated polyelectrolytes, fluorinate poly(vinylpyridine), poly(diallyldimethylammonium) (PDADMA), poly(styrene sulfonate) (PSS), 3,3,3-trifluoropropyltrimethoxysilan, tetramethylorthosilicate, lotus leaf powder, polymethylhydroxysiloxane, phenyl-substituted silica ormosil, stearic acid, polyvinylidene fluoride (PVDF), copper oxide, poly(ethylene terephthalate), polydimethylsiloxane, $WO_3$, $ZrO_2$, $ZnO$ and $CdS$, and polyoxometallates, or any other material known or yet to known materials.

The volume of the reaction chamber cavity 34 may be larger than the necessary volume needed for a reaction (e.g., between 3 mL and 15 mL The high density and gas impermeable material make the reaction chamber 10 sturdy. It also makes the measurement of the reactive gas more accurate, since little to no gas escapes. It is foreseen that at least one of the reaction chamber 10, surrounding container (not shown) about the controllable loader 18, 20, surrounding container (not shown) about the controllable collector 22, 24 may further include a layer of desiccant lining to keep the at least one of the reaction chamber 10, surrounding container (not shown) about the controllable loader 18, 20, surrounding container (not shown) about the controllable collector 22, 24, humidity free or resistant.

The bottom surface 43 may be tapered towards the center, wherein a bottom aperture 61 and plug 62 is situated. The bottom surface 43 of the inner surface 35 is illustrated as circular, but may be any geometric shape known, and is not meant to be limiting. The plug 62 seals the cavity 34 of the reaction chamber 10 by sealing the bottom aperture 61. The plug 62 may be connected to the controller 26 as will be further discussed below. The plug 62 may open and close to remove waste and fluid after the reaction and contaminant(s) have been measured (possible to another container).

A fluid sample connection assembly 53 runs from a first end 57 outside the reaction chamber 10 to within the cavity 34 of the reaction chamber 10 at a second end 56. The fluid sample connection assembly 53 includes a pipe 54, a valve 55, a sensor 58, and a connecting mechanism 60. The pipe 54 may be tubular and made from the same material as the reaction chamber 10 or may be made from a natural rubber, synthetic rubber, latex, silicone, ceramic, glass, metal or other materials known in the art for transporting fluid. The pipe 54 may be rigid and slanted downward so as to aid in directing the fluid sample 32 into the reaction chamber 10 or the pipe may be flexible and easily adaptable to connection to various fluid piping.

At or near the second end of the fluid sample connection assembly 53 may be the valve 55, the fluid sensor 58, and the connecting mechanism 60. The connecting mechanism may be situated on one end of the valve 55. The connecting mechanism 60 is adapted for directly connecting a pipe opening or at a valve (not shown) or a faucet (not shown) for home use. The fluid sensor 58 is in communication with the controller 26. For example, the controller 26 may respond after fluid is first detected entering the valve 55. Such a response will be further explained below. The valve 55 may be a solenoid valve which restricts backflow and closes after a predetermined volume of fluid (e.g. between 3 mL and 15 mL) has been introduced.

The fluid sample connection assembly 53 may further include a check valve (not shown), which allows the fluid to enter the reaction chamber 10 and then seals the check valve opening. The check valve may aid in ensuring that the reaction chamber 10 remains air-tight.

Figure 3B:
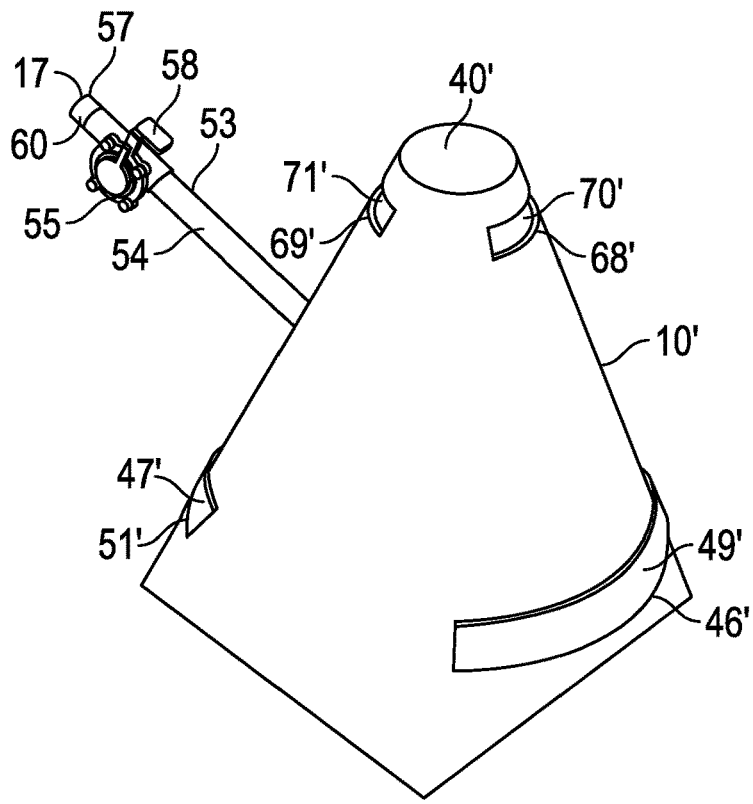
FIG. 3B is a perspective view of the reaction chamber in a second embodiment and the fluid entry valve.
Figure 8:
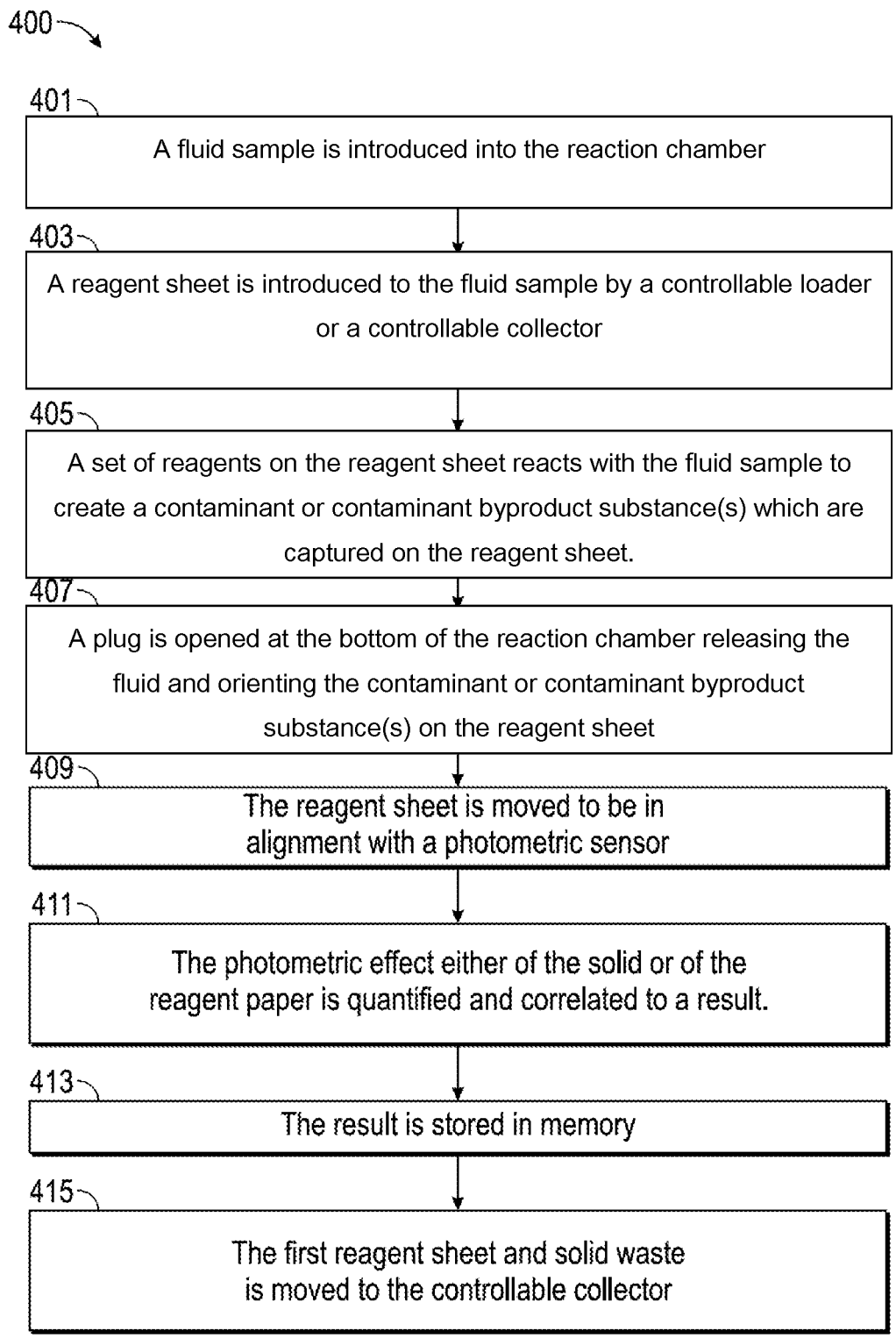
FIG. 8 is a block diagram of a method of sensing contaminants in a fluid.

With reference to FIG. 3B, a second embodiment of a reaction chamber 10' is illustrated for a contaminant sensor system 1' (FIG. 8). The reaction chamber 10' and other components of the system 1' are substantially similar to the counterparts in the system 1, except as specifically noted and/or shown, or as would be inherent. In this embodiment, the reaction chamber 10' is frusto-pyramidal shaped and the top surface 40' is closed or sealed off. Near the top surface 40' is situated a second set of opposed side apertures 68', 69'. Like the lower opposed side apertures 46', 47', each aperture 68', 69' may be identical to each other and are sized and shaped to allow a second reagent sheet 14' therethrough (FIG. 8). The opposed apertures 68', 69' are near enough to the top surface 40 such that when a predetermined amount of fluid sample is introduced into the reaction chamber 10', the second reagent sheet 14' is not situated too close to the first reagent sheet 12'. Each of the second set of opposed apertures 68', 69' may be substantially sealed by airtight chamber doors 70', 71' or other such low gas permeable means, for example, a butyl rubber sealant or rotary valve. The doors 70', 71' may be electronically connected to the controller 26' along with the doors 49', 51'. The bottom sides of the frusto-pyramid are illustrated as parallel with the first reagent sheet 12', but it is foreseen that the sides may be at an angle with respect to the first reagent sheet 12'.

Figure 3C:
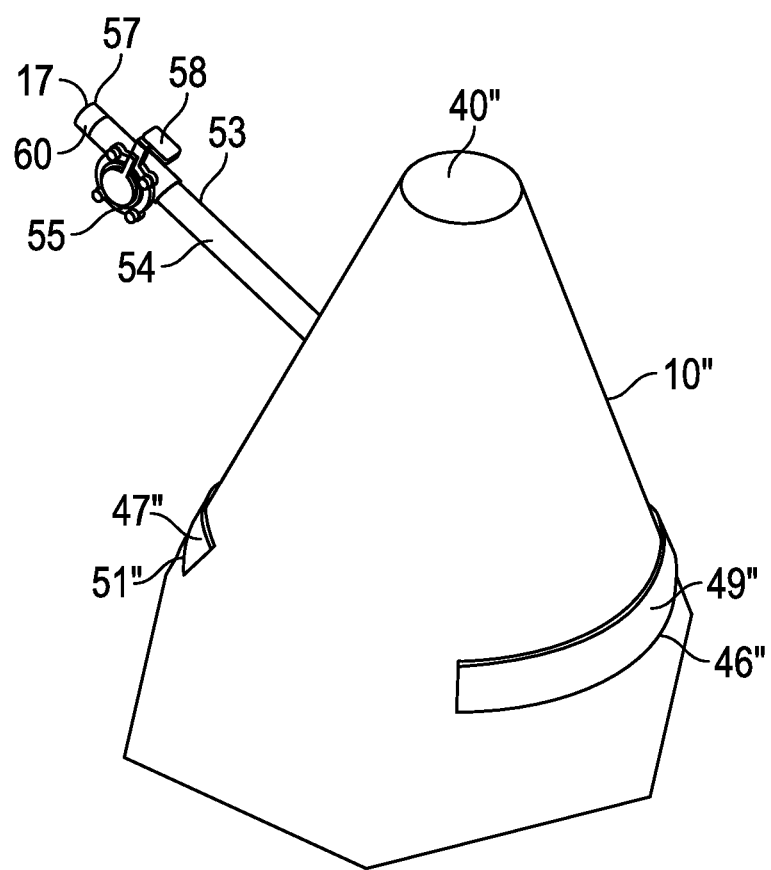
FIG. 3C is a perspective view of the reaction chamber in a third embodiment and the fluid entry valve.
Figure 9:
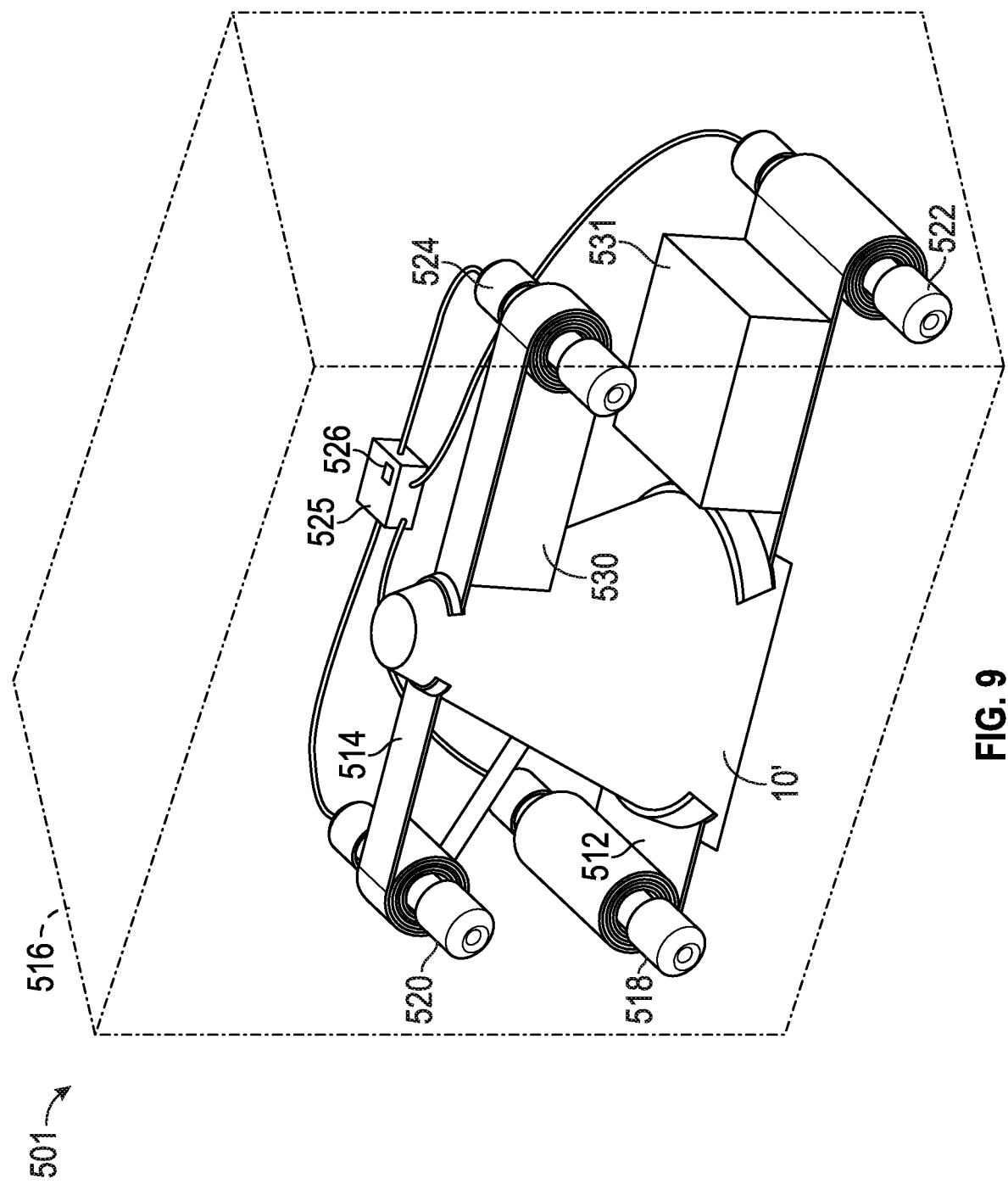
FIG. 9 is a perspective view of a contaminant sensor system according to third embodiment with the housing shown in phantom.

With reference to FIG. 3C, a third embodiment of a reaction chamber 10" is illustrated for a contaminant sensor system 1" (FIG. 9). The reaction chamber 10" and other components of the system 1" are substantially similar to the counterparts in the system 1, except as specifically noted and/or shown, or as would be inherent. In this embodiment, the reaction chamber 10" is frusto-hexagonally shaped and a top surface 40" is closed or sealed off. In this embodiment 1", there is only the first reagent sheet 12" and a second reagent sheet is not necessary, as will be further discussed below.

Figure 3D:
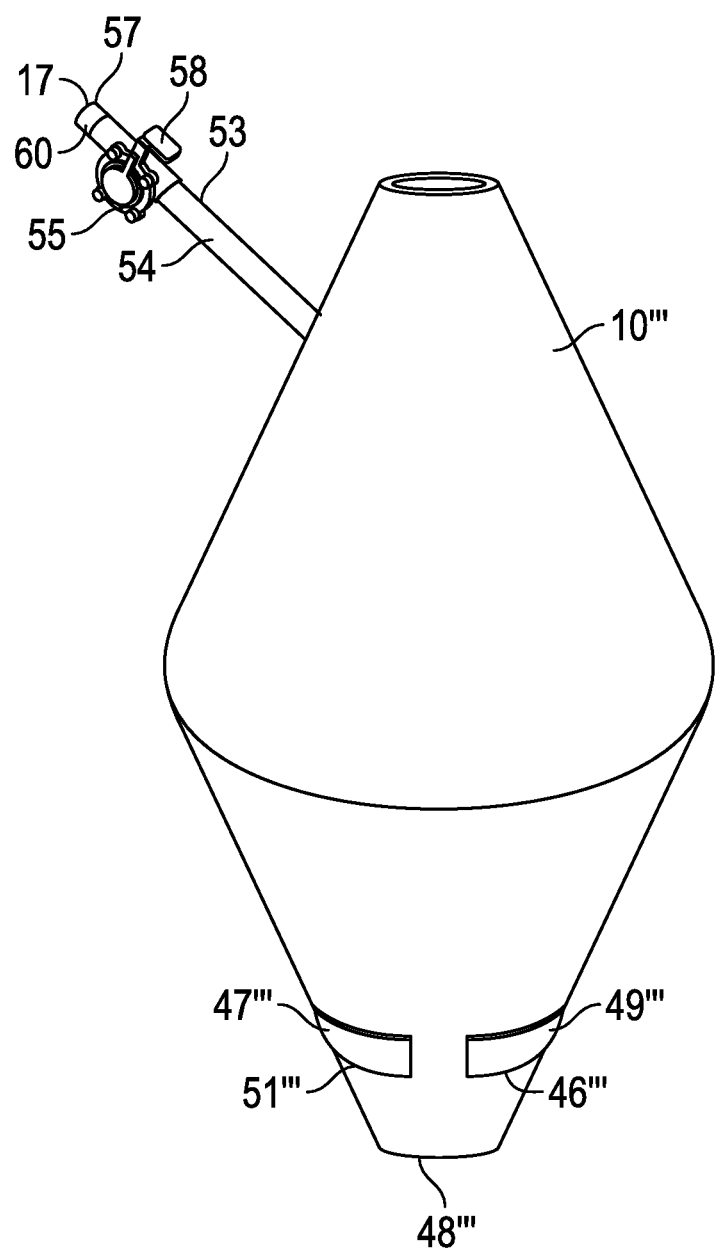
FIG. 3D is a perspective view of the reaction chamber in a fourth embodiment and the fluid entry valve.

With reference to FIG. 3D, a fourth embodiment of the reaction chamber 10''' is illustrated for a contaminant sensor system (not shown). The reaction chamber 10''' and other components of the system substantially similar to the counterparts in the system 1, except as specifically noted and/or shown, or as would be inherent. The reaction chamber has an exterior of two opposed frusto-cones stacked base to base creating a frusto-diamond-like cross section. In this embodiment, it is envisioned that the bottom may have a bottom aperture as in the top aperture 42", such that first reagent sheet seals a bottom aperture or it may be closed off as illustrated, where a first reagent sheet may pass through the downward directed frusto-cone near a bottom 48''' thereof and the second reagent sheet either passes through the upward directed frusto-cone or seals a top aperture 42''' as illustrated.

Figure 4:
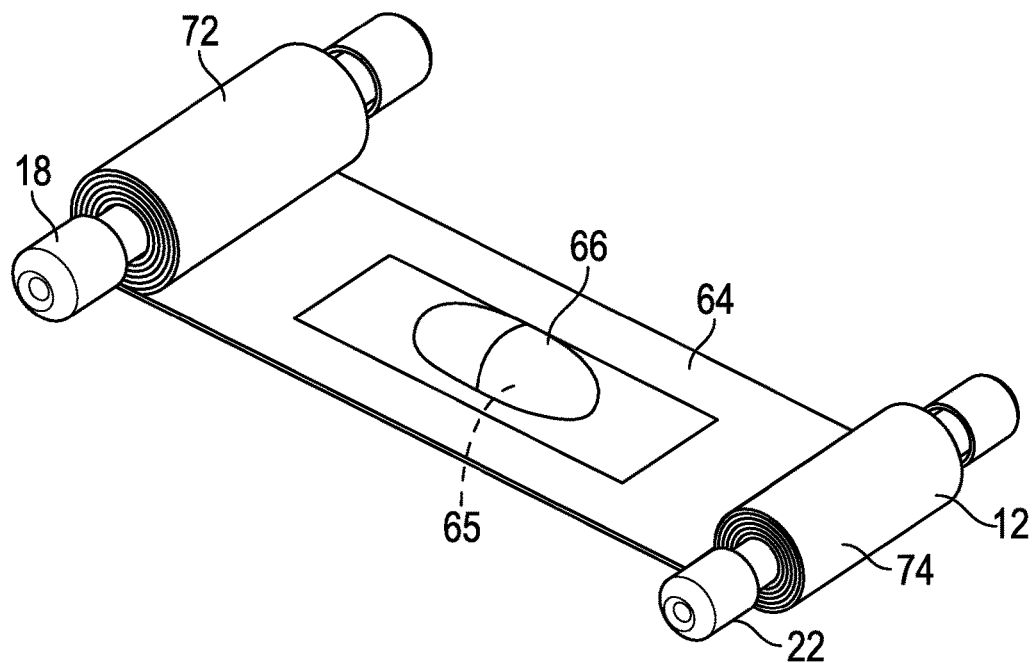
FIG. 4 is a perspective view of the first reagent roll and polymer.

Referring now to FIG. 4, the first reagent sheet 12 is illustrated. The reagent sheet 12 may be made from at least one of the following: paper, plastic, metal, at least one natural polymer, at least one synthetic polymer, electrospun nanofiber and glass. A portion of strip 64 of the first reagent sheet 12 is situated within the reaction chamber 10, the first reagent sheet 12 being positioned through the apertures 46, 47 and sealed within the cavity 34. It is foreseen that the first reagent sheet 12 may further include wings that are initially folded prior to entry into the reaction chamber and become unfolded when within the reaction chamber 10. A purpose of the wings may be to cover the entire bottom portion 43 of the inner surface 35.

A first set of reagents (including compounds that may be added to enhance a reaction) 65 are sealed onto the first reagent sheet 12. This may be accomplished by a single polymer, a co-polymer, or a composite 66. In certain embodiments, the polymer, co-polymer or composite forms a matrix, packet, envelope or capsule with the reagent sheet holding the reagents in place. The portions 64 with a first set of reagents sealed on the strip are evenly spaced throughout the entire sheet 12 to ensure only one packet 66 is in the reaction chamber 10 at a time. The polymer 66 reacts with the fluid 32 to release the first set of reagents 65 and therein react with the fluid sample 32. This may be accomplished by expansion, dissolving, or other means known in the art. A non-exhaustive list of reagents 66 in the first set of reagent includes: sulfamic acid, hydrochloric acid, tartaric acid, sodium borohydrate, potassium permanganate, potassium peroxodisulfate, molybdenum blue, sodium phosphate dibasic, potassium monopersulfate, arsenomolybdic acid, polyoxometallates, rhodamine, coumarin, fluorescein, lead acetate, nickel sulfate, EDTA, NEDA, sulfanilic acid, salicylic acid, methylene blue, tetrachloroauric acid, trihydrate, zinc acetate dehydrate, curcumin, difluoroboron curcumin, zinc, gold, dithiothreitol, N-acetylcystein (NAC), N-acetylcystein amide (NACA), cysteine, glutathione, glutathione reductase, glutathione transferase, $TiO_2$, maleic acid, sulfur anions, dithiazone compounds, diethyldithiocarbamate compounds, diphenylcarbazone compounds, porphyrin compounds, cyanide, mercaptonicotinic acid, sodium sulfide, metal-oxo clusters, MLPOM, methanol, polyoxometalates, 1-(4-iso-thiocyanobenzyl)-ethylenediamine-N,N,N0,N0-tetraacetic acid (ITCBE), 1-(4-aminobenzyl)-ethylenediamine-N,N0,N0-tet-raacetic acid (aminobenzyl-EDTA), 6-mer-captonicotinic acid, tryptophane, glycine, Lys, mercaptoundecanoic acid, mercapto aliphatic acid, PDCA, dithioerythritol, 3-nitro-1H-1, 2, 4-triazole, 2-amino-2-hydroxymethyl-propane-1,3-diol, 4,4-dipyridyl, thymine, thiourea, 2-mercaptoethanol, 11-mercapto-undecyl)-trimethyl-ammonium, poly(diallyldimethylammonium) chloride, 4-mercaptobutanol, 6-mercapto-hexanol, 11-mercaptoundecanol, N-acetyl-L-cysteine, N-acetyl-L-Cysteine Amide, adenosine monophosphate, 11-mercaptoundecanoic, MPA, DTET, MPA/AMP, Thymine-SH, Tris/NTA, DPY, Pyridine, Thymine-AuNPs, Thiourea-AuNPs, HS-EG, 4-Mercaptobutanol, MTA, Cysteine, Tween 20, AA, hydrogen tetrachloroaurate(III) hydrate, sodiumborohydride, Alizarin dye, 3-mercaptopropionic acid (MPA), 2,6-Pyridinedicarboxylic acid, HEPES buffer solution, sodium chloride, trisodium citrate 13ehydrate (TSC), 4-amino-3-hydrazino-5-mercapto-1,2,4-triazole (Purpald), hydrogen tetrachloroaurate(III) tetrahydrate, citric acid, thiophosgene, silver perchlorate hydrate, calcium perchlorate tetrahydrate, cadmium perchlorate hydrate, cobalt chloride hexahydrate, copper(II) tetrafluoroborate, iron(II) tetrafluoroborate, iron(III) chloride hexahydrate, mercury(II) perchlorate hydrate, magnesium perchlorate hexahydrate, nickel(II) acetate tetrahydrate, lead(II) perchlorate trihydrate, zinc tetrafluoroborate hydrate, Manganese sulfate, tris(hydroxymethyl) aminomethane (Tris), 2-(N-morpholino)ethanesulfonic acid, dipenylcarbazide, amonium hydroxide, ammonium sulfate, sodium bicarbonate, sodium carbonate, 1-diphenylcarabzide, sulfuric acid, citrate, ascorbic acid, potassium dichromate, sodium sulfite, 4-Aminoantipyrine, 4-aminoantipyrine, 1-naphthol, dopamine dithiocarbamate (functionalized on AuNP, AgNP), tris-tricine buffer, resorcinol, ammonia, perylene bisimide chromophore, aldazine, (4-diethylamino)-salicylaldehyde-azine, 8-hydroxyjulolidinal-azine, 1-phenyl-3-methyl-4-benzoyl-5-pyrazolone, flavonoid-morin, hydroxylamine, tetrakis (4-carboxyphenyl) porphyrin, triarylamine derivative ETPA, acetonitrile, 5-Chloro-2-((E)-((E)-3-(4-(dimethylamino)phenyl)allylidene)amino)phenol, Iridium (III), thiosulfate, cysteamine, 2,2'-thiodiacetic acid, 4-mercaptobenzoic acid, D-penicillamine, Boronic Acid, bisboronic acid, ((E)-9-((2-hydroxynaphthalen-1-ylimino) methyl)-1,2,3,5,6,7-hexahydropyrido[3,2,1-ij]quinolin-8-ol), acylthiosemicarbazide bearing compounds, nitrophenyl bearing compounds, gadolinium, N-isopropylmethacrylamide, dicyanomethylene-4H-pyran containing compounds, bis-rhodamine, indolylmethane, 4-amino-1,8-naphthalimide, o-phenylenediamine, Potassium persulfate, dithiotheitrol, polyaniline (PANI) emeraldine salt, camphor sulfonic acid, polystyrene modified gold nanoparticles, acetic acid, alfusone, Imidazole, acetone, polyethyleneimine, poly (ethylene glycol), perfluoroalkyl-terminated (F-thiols) alkanethiols, naphthylethylenediamine dihydrochloride, sulphanilamide, phosphoric acid, phenyl-alcohol, Sodium nitroprusside, trisodium citrate, sodium hypochlorite, NADPH, 2,3-diaminonaphthalene, diaminofluoroscein-2, azide, nitrate reductase, hodamine B, purine-nucleoside phosphorylase, xanthine oxidase, 3-(4',5'-dimethyl-2-thiazolyl)-2,4-diphenyl-2H-tetrazolium bromide, maltose, maltose phosphorylase, glucose oxidase, Horseradish peroxidase, potassium antimony tartrate, ammonium molybdate, Protein phosphatase, ammonia heptamolybdate, sodium silicate, sodium hydroxide, zincon, ethanol, ethylenediaminetetraacetic acid disodium salt dehydrate (Na2-EDTA), tetrabutyl titanate (TBT), hexadecyltrimethoxysilane (HT-DES), tetrabutylammonium, 4☐methyl☐2☐pentanone, α☐furyl dioxime (FDO) chelate, 4-methyl-2-pentanone methyl isobutyl ketone, MIBK, sodium bismuthate, tammonium peroxydisulfate, potassium periodate, potassium nitrite, potassium hydrogen sulfate, potassium iodide, hydrobromic acid, phenylfluorone, hydrofluoric acid, silver nitrate, 4-Phenylazo-m-phenylenediamine (Chrysoidine G, CG), lithium chloride, iron(II) chloride tetrahydrate, magnesium(II) chloride hexahydrate, manganese(II) chloride tetrahydrate, aluminum(III) chloride hexahydrate, (polyvinylpyrrolidone), ethylene glycol, polyvinyl alcohol, NaDDBS, polyoxyethylene(20)sorbitan monolaurate (TWEEN 20), cetyltrimethylammonium bromide (CTAB), boric acid, guanidinium chloride, sodium perchlorate, tris(hydroxymethyl)aminomethane (Tris), urea, ethanolamine, isopropanol, zinc acetate di hydrate, zinc nitrate hex hydrate [$Zn(NO_3)_{26}$ $H_2O$], hexamethylenetetramine [$C_6H_{12}N^4$], ionophore, sodium tetraphenyl-borate (NaTPB), di-n-butyl-phathalate (DBP), poly vinyl chloride (PVC), and tetrahydro-furan (THF). This list would include nanoparticles, nanoclusters, catalytic DNA molecules, protein functionalized nanoparticles, DNA functionalized nanoparticles, metal organic frameworks, metals, lanthanides, organic reagents, biological compounds, organonucleotides, organopeptides, fluorescent dyes, immunosensors, and inorganic reagents.

Before or as a new test is initiated, the controllable loader 18 loads a predetermined increment of the sheet 12 to allow the portion 64 of first reagent sheet 12 to enter the reaction chamber 10. The increment is based upon the size and shape of the reaction chamber 10. In the illustrated example, the controllable loader 18 is a spindle. Another example of such would be a cartridge (not shown) holding a plurality of portions 64 of the first reagent sheet 12. It is foreseen that the controllable loader 18 may be any type of loader that is controllable via the controller 26, houses a section 72 of unused portions of the first reagent sheet 12 and is connected to a controllable collector 22. The spindle 18 is in communication with the controller 26 as will be further discussed below.

A section 72 of unused first reagent sheet 12 is shown rolled or wound about the spindle 18. The first reagent sheet 12 enters the reaction chamber 10 through a shutter door 49, 51. It is foreseen that wax (not shown) can be permeated through the sheet at various intervals to ensure that water does not saturate the next portion 64 of the first reagent sheet 12. It is also foreseen that the first few portions 64 of the first reagent sheet 12 may not have any reagent on the sheet 12 to allow for the initial winding onto the controllable collector 22.

The first reagent sheet 12 serves a second purpose. After a fluid sample 32 is done being tested, the bottom aperture 61 is opened and the fluid drains through the sheet before exiting the aperture 61, leaving the solid waste (not shown) that formed during the reaction attached to the first reagent sheet 12. The solid waste, which remains on and adheres to the first reagent sheet 12 and a used section 74 of the first reagent sheet 12 is pulled through the reaction chamber 10 by at least one of the controllable loader 18 (i.e. pushed) or the controllable collector 22 (i.e. pulled). Likewise, the roll 72 may be installed either way such that at least one of the controllable loader 18 or controllable collector 22 is rotated either clockwise or counterclockwise to extend the roll unused portion 72. The waste and used section 74 is collected outside of the reaction chamber 10 into the controllable collector 22. This solid waste and used section 74 is stored until the entire first reagent sheet 12 is changed after depletion or significant depletion of unused sections 72. In the illustrated example the solid waste and used section 74 is wound about a second spindle or controllable collector 22. It is foreseen that the used section 74 and/or the unused section 72 may be housed in a desiccant chamber or lined with a desiccant lining to aid in drying.

Figure 5:
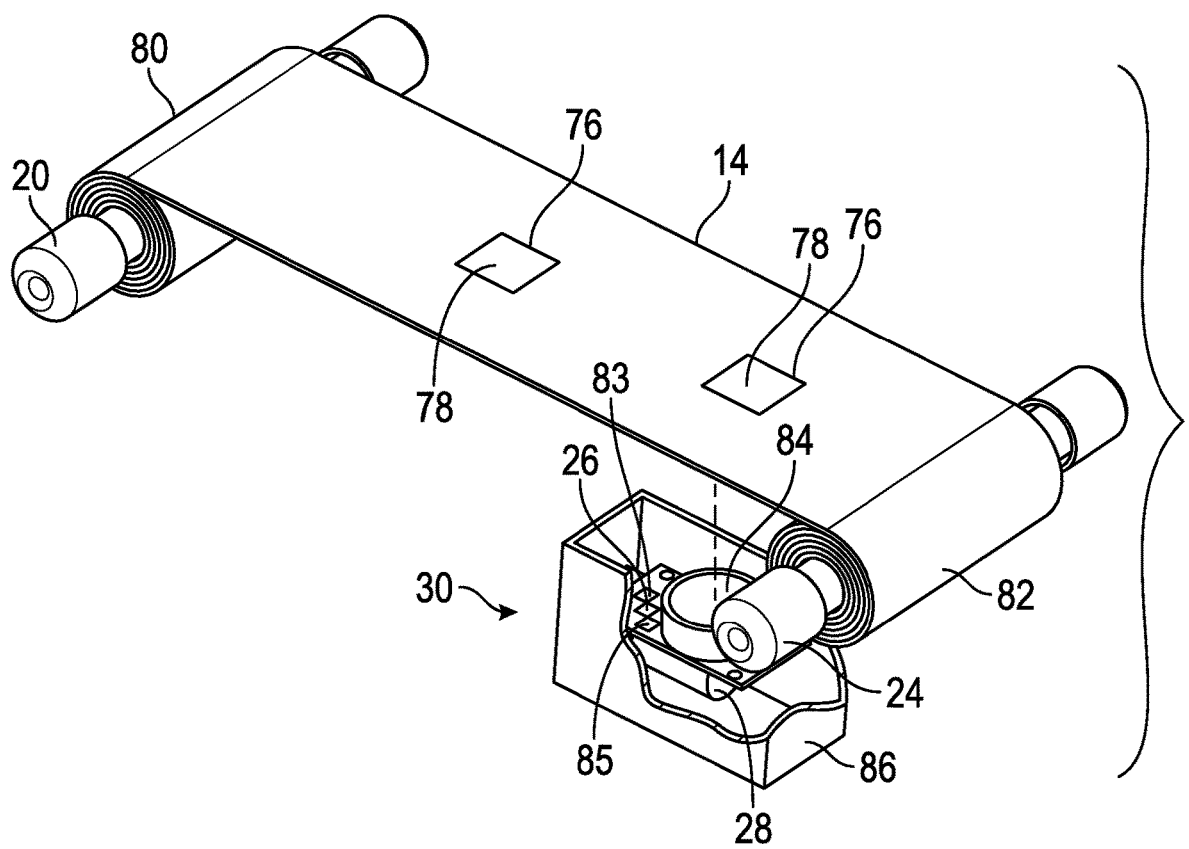
FIG. 5 is perspective view of the second reagent roll and the photometric chamber with portions of the photometric chamber cut away.

With reference to FIG. 5, the second reagent sheet 14 and the photometer assembly 30 are illustrated. The second reagent sheet 14 may be made from at least one of the following: paper, plastic, metal, at least one natural polymer, at least one synthetic polymer, electro spun nanofiber and glass. A portion or strip 76 of the second reagent sheet 14 is situated to cover the top aperture 42 of the reaction chamber 10. The stopper 44 being positioned on a top surface to the second reagent sheet 14 to seal the cavity 34 of the reaction chamber 10.

A second set of reagents 78 (including compounds that may be added to enhance a photometric effect reaction) are embedded into the second reagent sheet 14. This may be accomplished by a single polymer, a co-polymer, or a composite 78. The portions 76 with the second set of reagents 78 embedded on the strip may be evenly spaced throughout the entire sheet 14 to ensure only one second set of reagents 78 is covering the top aperture 42 of the reaction chamber 10 at a time or the second set of reagents 78 could be mixed equally throughout the sheet 14. The second set of reagents reacts with a contaminant byproduct(s) produced from a reaction with the first set of reagents to cause a photometric effect change in the second reagent sheet 14 itself. Such a photometric effect may be a change in color, fluorescence, reflectance or absorbance of ultra-violet (UV), and reflectance or absorbance of infrared (IR). A non-exhaustive list of reagents 78 in the second set of reagent includes: dithiothreitol, N-acetylcystein (NAC), N-acetylcystein amide (NACA), cysteine, glutathione, curcumin, difluoroboron curcumin, silver nitrate, mercuric bromide, silver diethyldithiocarbamate, mercuric halide, sodium perbordate, azure B, methanol, persulfates, permanganates, nitric acid, sulphuric acid, and aqua regia. This list would include nanoparticles, nanoclusters, catalytic DNA molecules, protein functionalized nanoparticles, DNA functionalized nanoparticles, metal organic frameworks, metals, lanthanides, organic reagents, biological compounds, organonucleotides, organopeptides, fluorescent dyes, immunosensors, and inorganic Reagents.

Before or at the moment a new test is initiated, like the first controllable loader 18 with the first reagent sheet 12, the second controllable loader 20 loads a predetermined increment of sheet 14 to allow the portion 76 of second reagent sheet 14 to cover the top aperture 42 of the reaction chamber 10. In the illustrated example, the second controllable loader 20 is a spindle. Another example of such would be a cartridge (not shown) holding a plurality of portions 78 of the second reagent sheet 14. It is foreseen that the second controllable loader 20 may be any type of loader that is controllable via the controller 26 and houses a section 72 of unused portions of the second reagent sheet 14, and is connected to the second controllable collector 24. The third spindle 20 is in communication with the controller 26 as will be further discussed below.

A section 80 of unused second reagent sheet 14 is shown rolled or wound about the spindle 20. It is foreseen that the first few portions 76 of the second reagent sheet 14 may not have any reagent embedded on the sheet 14 to allow for the initial winding onto the controllable collector 24. After the second set of reagents 78 reacts with the contaminant byproduct(s) or nothing, the now used section 82 of the second reagent sheet 14 is pulled away from the top aperture 42 of the reaction chamber 10 by at least one of the controllable loader 20 (i.e. pushed) or the controllable collector 24 (i.e. pulled) to be in position with the photometer assembly 30. The second reagent sheet 14 may be installed such that at least one of the spindles 20, 24 rotates either clockwise or counterclockwise to extend and provide the next portion 76. Once the photometer assembly 30 has concluded its photometric analysis, as will be further explained below, the used section 82 of the second reagent sheet 14 is again pulled away from the photometer assembly 30 and collected outside of the reaction chamber 10 onto the controllable collector 24. In the illustrated example the used section 82 is wound about a fourth spindle or controllable collector 24.

The photometer assembly 30 may include the controller 26, the power source 28, memory 83, a photometric sensor 84, and housing 86. The controller 26, the power source 28, the memory 83, the sensor 84 are envisioned to be positioned within the housing 86. The housing 86 may have one or more openings, at least one for the photometric sensor 84. It is foreseen that the sensor 84 may be located within the reaction chamber 10.

Figure 6:
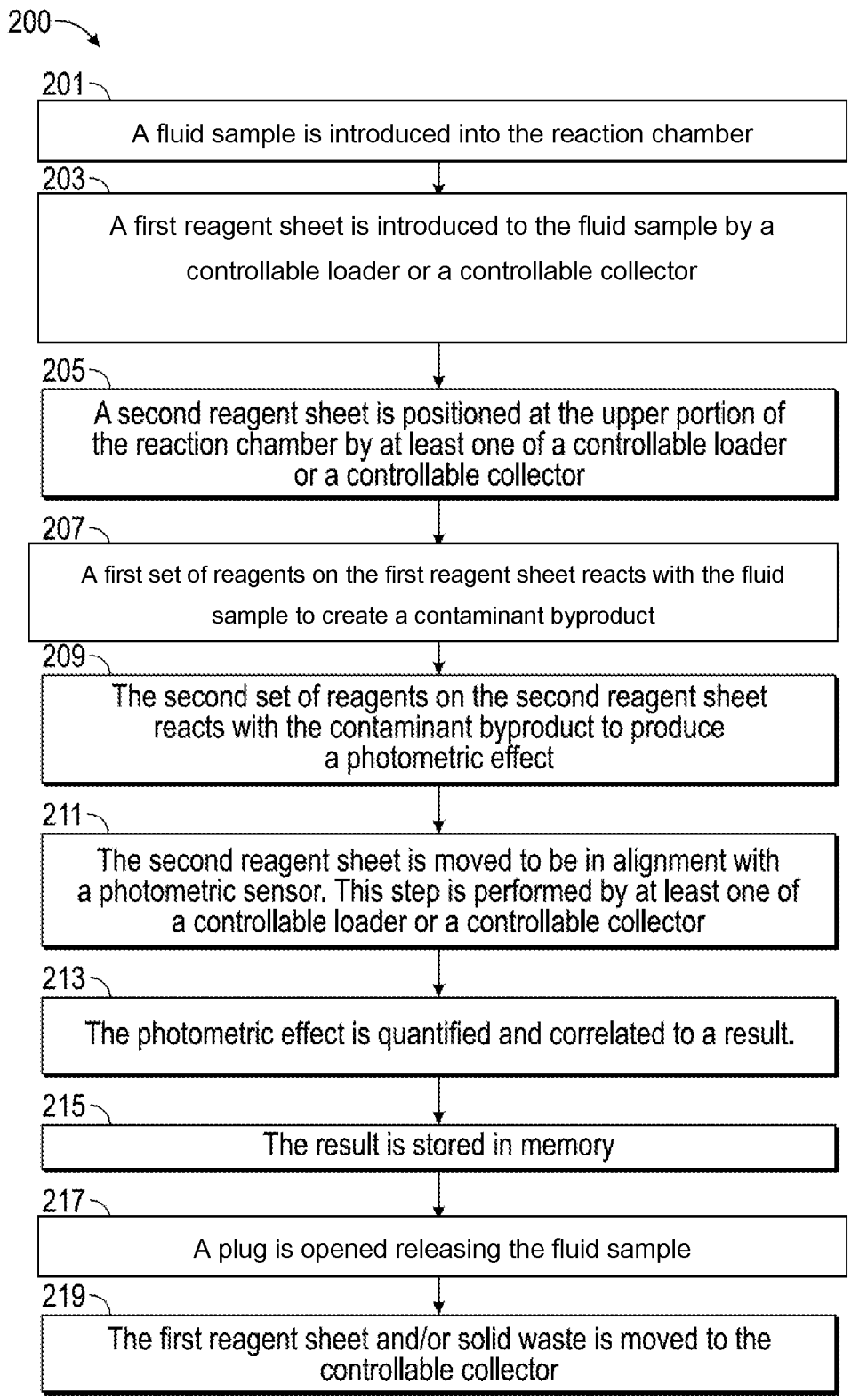
FIG. 6 is a block diagram of a method of sensing contaminants in a fluid.
Figure 7:
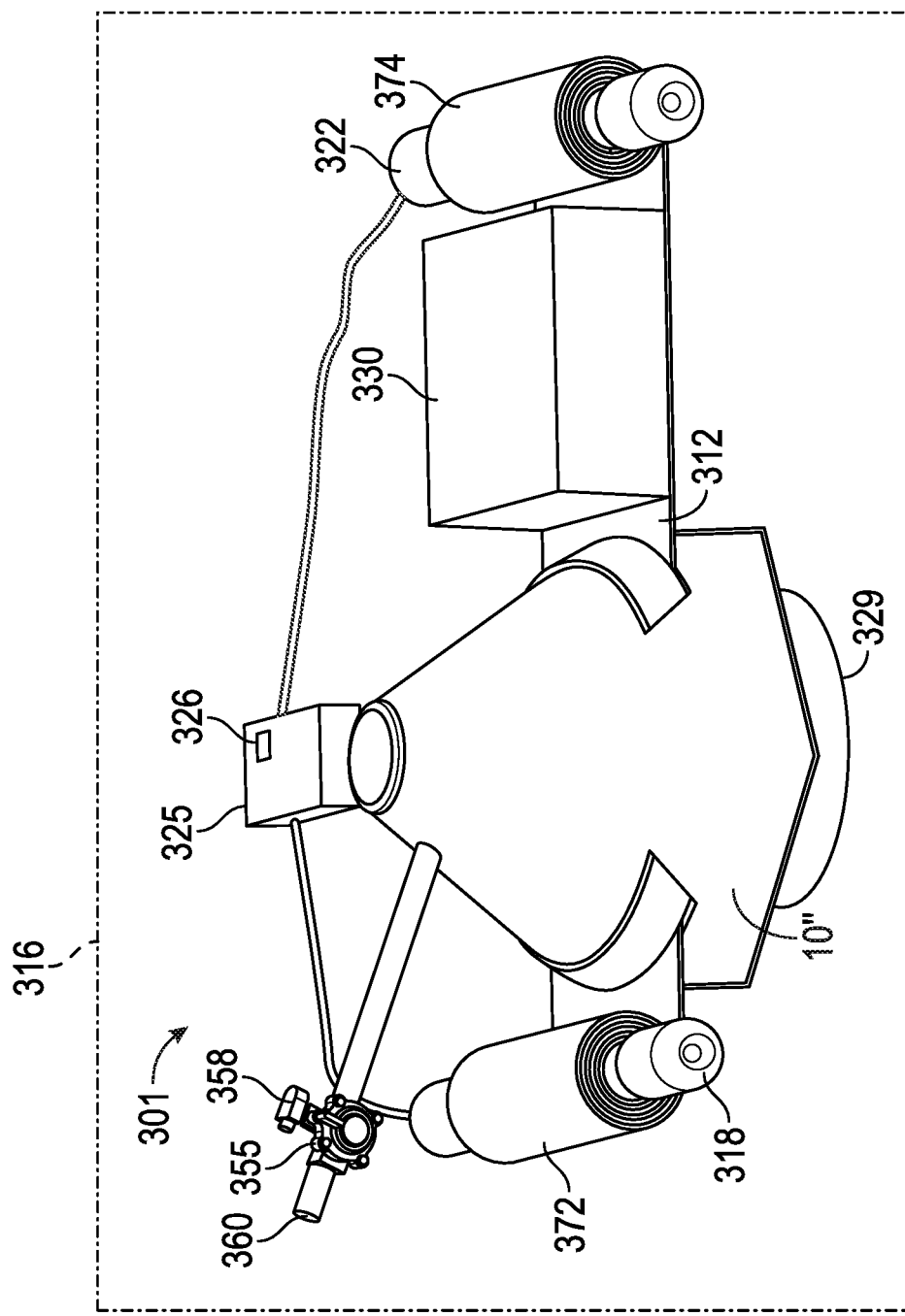
FIG. 7 is a perspective view of a contaminant sensor system according to second embodiment with the housing shown in phantom.

The processor 26 (or "controller" or "master board") may be any appropriate device, whether now existing or later developed, which performs the operations specified by the various programming used by the system 1 and method. The controller 26 may be electronic circuitry located on a common chip or circuit board, or may be a distributed processor such that one portion of the processor is physically separate from another portion of the processor (i.e. not a part of the photometer assembly 30). Discrete processing devices may be linked together (e.g., over a network) and collectively form the controller 26. While this document shall often refer to elements in the singular, those skilled in the art will appreciate that multiple such elements may often be employed and that the use of multiple such elements which collectively perform as expressly or inherently disclosed is fully contemplated herein. The processor 26 is in data communication with the photometric sensor 84, the memory 83, transceiver 85, and the spindles 18, 20, 22, 24 by means of motor 25 control, and may further be in data communication with other peripherals (e.g., doors 49, 51, 70, 71, the water sensor 58, stopper 44, control valve 55, and the plug 62) and the at least one motor 25 that control these peripherals to control the process of the method of the contaminant system 1 as will be further discussed below (FIGS. 6 and 7).

The transceiver 85 may include a transmitter (or "antenna"). The antenna may be situated outside the housing 86, as the housing 86 may act as a shield to RF communications. The antenna may be a part of circuitry located in the photometer assembly 30. The transceiver 85 communicates directly and/or over a wireless communication infrastructure with other devices configured to receive such wireless communication to provide data from the photometric sensor 84. In direct wireless communications, the transceiver 85 may include baseband processing circuitry to convert data into a wireless signal (e.g., radio frequency (RF), Bluetooth, ZigBee, Radio Frequency Identification (RFID), infrared (IR), ultrasound, near field communication (NFC), et cetera) and the transmitter 85 transmits the wireless signal. When a second wireless transceiver (not shown) is within range (i.e., is close enough to receive the wireless signal at a sufficient power level), it receives the wireless signal and converts the signal into meaningful information (e.g., location data, analysis results, etc) via baseband processing circuitry (e.g., through an application on a phone, computer, notepad, etc.).

For indirect wireless communication or communication via a wireless communication infrastructure, the first wireless transceiver 85 transmits a wireless signal to a base station or access point, which conveys the signal to a wide area network (WAN) and/or to a local area network (LAN). The signal may traverse the WAN and/or LAN to a second base station or access point to send the signal to the second wireless transceiver or it may traverse the WAN and/or LAN directly to the second wireless transceiver. Examples of wireless communication via an infrastructure include cellular satellite/tower, IEEE 802.11, public safety systems, et cetera.

The memory 83 may include volatile and non-volatile memory, and any appropriate data storage devices whether now existing or later developed may be used. Further, the memory 83 may be a unitary memory in one location, or may alternately be a distributed computer memory such that one portion of the computer memory is physically separate from another portion of the non-transitory computer memory. Example memory devices which may be employed include SRAM, DRAM, EPROM, EEPROM, Flash, magnetic, rotating media, ferromagnetic, and U3 smart drives. The memory 83 is in communication with the controller 26 for providing data to and receiving data from the controller 26. In some embodiments, data may be encrypted to prevent disassembly and reverse engineering.

The memory 83 may include, for example, a program storage area (for storing software or "instructions") and a data storage area (for storing analysis results, location data, and other data). The controller 26 is configured to retrieve from memory 83 and execute, among other things, instructions or modules related to the control processes and methods described herein. The controller 26 is connected to the memory 83 and may execute software instructions or modules that are stored in a RAM of the memory 83 (e.g., during execution), a ROM of the memory 83 (e.g., on a generally permanent basis), or another non-transitory computer readable medium such as another memory or a hard disc or database. For example, software can be stored in the internal memory of the controller board 26. The controller 26 can have part of its operations dedicated to a data transfer function between the photometric sensor 84 to the memory 83, and another part dedicated to the moving or rotation of the spindles 18, 20, 22, 24; or can have the two functions in separate controllers (i.e., a data transfer function controller and a mechanical device controller).

The power source 28 may be located within the photometric housing 86 or may be located remotely. The power source 28 may be the power source 28 of the photometer assembly 30 or of the entire system 1 itself. The power source 28 may be at least one or more of: a battery or batteries, a computer battery through a USB connection, a fuel cell, a motion-based generator that collects and stores power based on the rotation of the spindles 18, 20, 22, 24, a solar cell, or other source of electricity means known in the art. For example, the system 1 may be hard wired to an outlet, which may provide the system 1 with the required energy (e.g., 8V to 24V, 110V, or 220V) for operation. However, it may be beneficial for the system 1 to include means for storing power, both in situations in which the system 1 is hard wired to an outlet, and where the system 1 receives its power from an outside source. In such cases, the power source 28 may for example be capacitors or a back up battery, such as NiCd (nickel-cadmium), NiZn (nickel-zinc), NiMH (nickel-metal hydride), or lithium-ion. The battery 28 may be configured to receive electrical energy from an outlet during hours when rates may be lower due to lower demand, and then use the energy during the day, when rates may otherwise be higher. Alternately, or additionally, the battery may store energy from other sources which may then be converted into electrical energy for use by the system. For example, the system may be able to capture solar energy through a photo-voltaic cell. The system 1 may, for example, provide an indication (e.g., a sound, a displayed message, a flashing LED, etc.) to a user that the battery 28 is low or that the capacitor is being used and the power source 28 should be replaced soon.

The photometric sensor 84 detects changes in a single photometric effect (e.g. color) or multiple photometric effects at the same time. For example, such a detector 84 may be a light emitting diode that obtains red, green, and blue reflectance photometric values of the used section 82 of the second reagent sheet 14. In this example, the detector 84 may work by illuminating the used section 82, one LED at a time. A broad spectrum photodiode measures the light that is reflected back (i.e. in a range of 320-1050 nm). The output voltage, which is linear to irradiance is inputted to a controller 26. These voltage readings are then transmitted as data via the transceiver 85 to a computer or smart device via direct or indirect communication. Using a light reflectance approach, the contamination of the fluid can be calculated and detected (i.e. as low as 5 μg/L with an accuracy of ±5%). If the owner of the data chooses to release their data, a map of the geo-temporal contaminant contamination in various regions from various systems (not shown), and the geographical region as a whole, can be created. This big data can be used to better understand, track, and solve systemic contamination, for example in drinking water.

FIG. 6 illustrates some steps 200 that may be employed by the various systems described herein to test for a contaminant in a fluid. In step 201, a fluid sample 32 is introduced into the reaction chamber 10. A valve 55 may control the exact amount of fluid to enter the reaction chamber 10, therein maintaining consistency in results. In step 203, a first reagent sheet 12 is introduced to the fluid sample 32 by a controllable loader 18 or a controllable collector 22. Step 203 may be such that the controller 26 controls at least one motor 25 that operates either controllable loader 18 or a controllable collector 22. This step may occur upon sensing that fluid (i.e. from fluid sensor) has entered the reaction chamber 10, at a time after, or before. At step 205 a second reagent sheet 14 is located at the upper portion 39 of the reaction chamber 10 by at least one of a controllable loader 20 or a controllable collector 24. Step 205 may be such that the controller 26 controls at least one motor 25 that operates either controllable loader 20 or a controllable collector 24. Step 205 may occur after, at the same time, or before steps 201 and 203. In some embodiments, the second reagent sheet 14 will cover a top aperture 42, and a stopper 44 will engage the top surface 40 and the second reagent sheet 14 to seal the reaction chamber 10.

At step 207, a first set of reagents on the first reagent sheet 12 react with the fluid sample to create a contaminant byproduct(s) or gas that rises towards the top surface 40 of the reaction chamber 10. At step 209, the second set of reagents on the second reagent sheet 14 react with the contaminant byproduct(s) or gas to produce a photometric effect. At step 211, the second reagent sheet 14 is moved to be in alignment with a photometric sensor 84. This step is performed by at least one of a controllable loader 20 or a controllable collector 24. At step 213, the photometric effect is quantified and correlated to a result, i.e. contaminant concentration or level in the fluid sample 32. At step 215, the result is stored in memory. At step 217, a plug is opened releasing the fluid. At step 219, the first reagent sheet 12 and solid waste is moved to the controllable collector 22. The controllable collector 22 may be a spindle that rotates to roll the first reagent sheet about the spindle 22.

An example of this method 200 is as follows. The method 200 for detecting a contaminant, arsenic is initiated after water is first detected entering a solenoid valve 55 that is connected to the system 1. This detection occurs with a shorting analog water sensor 58. The valve 55 opens when water is introduced and closes after a fixed volume of the sample 32 has passed through the valve. The water sample 32 moves from the valve to the reaction chamber 10 through a check valve (not shown), which allows the water to enter the chamber and then reseals the valve opening (not shown).

A controller 26 controls a motor 25 that are connected with either two controllable spindles that load or two controllable spindles that collect a respective first and second reagent paper 12, 14. The controller 26, such as an Arduino Pro microcontroller controls the motor 25 to rotate a spindle 18, 20, 22, 24 to move the first reagent paper 12 into the reaction chamber 10 and the second reagent paper 14 at the top 40 of the reaction chamber 10. The second reagent paper 14 covering a top aperture 42 and a stopper 44 engaging the top surface 40 and the second reagent sheet 14 seals the reaction chamber 10.

The first reagent paper 12 includes a set of reagents 65, in this case, sulfamic acid (pKa 1.0) and zinc. The first set of reagents 65, sulfamic acid and zinc, are sealed onto the paper 12 using polyvinyl alcohol (PVA). PVA is a polymer 66 that quickly dissolves when it is in contact with water. The regions 64 with reagent sealed on paper 12 are evenly spaced throughout the roll to ensure only one packet is in the reaction chamber 10 at a time. The chemical reactants that are sealed within the PVA are released when the water sample comes in contact with the strip-thereby initiating the reaction (a) below. If there is arsenic present in the water sample 32, the overall chemical reaction within the reaction chamber 10 is:

a. Formation of arsine gas:

$$Zn(0) \rightarrow Zn^{2+} + 2e^- \quad (1)$$

$$2H^+ + 2e^- \rightarrow H_2 \quad (2)$$

$$As(V) + 2e^- \rightarrow As(III) \quad (3)$$

$$As(III) + 3e^- \rightarrow As(0) \quad (4)$$

$$As(0) + 3e^- + 3H^+ \rightarrow AsH_3 \quad (5)$$

The second reagent paper 14 includes a second set of reagents including silver nitrate. The paper 14 is created from electrospun nanofibers. Nanofibrous material has a higher surface area to volume ratio and will allow more silver nitrate to react with the arsine, inducing a more intense color change. The silver nitrate is impregnated on the paper 14 to react with arsenic hydride gas to form a color change with arsine gas, as well as neutralize the gas, see reaction (b) below.

b. Arsine gas reacts with silver nitrate:

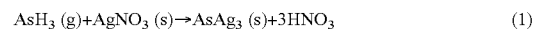

$$AsH_3\,(g) + AgNO_3\,(s) \rightarrow AsAg_3\,(s) + 3HNO_3 \quad (1)$$

The second reagent paper 14 is pulled forward at timed increments for a new sample to be tested and to be aligned with a photometric assembly 30. When arsine gas, $AsH_3$ (g) reacts with silver nitrate, $AgNO_3$, it creates a strong color change of varying shades of brown and grey. When using between 0.1% and 0.2% (m/v) silver nitrate on a strip 14, there is a very sensitive detection range of arsenic concentrations between 0.01-20 ppb. The red, green and blue reflectance values of the colored spot are detected by the photometer sensor 84 and the data is recorded in memory 84 by the controller 26. This color change is calibrated from a voltage to arsenic concentration and this data is saved to computer or smart device 83 by the controller 26.

After the water sample 32 is tested, the reaction chamber 10 is flushed by a bottom aperture 61 opening, causing the water's ejection from the reaction chamber 10. The solid waste, which remains on and adheres to the first reagent paper 12, is pulled through the reaction chamber 10 by the motor 25 control of one of the spindles 18, 22, and is wound outside of the chamber 10 on a spindle 22. This solid waste and first reagent paper 12 is stored in a roll 74 until the entire roll of reagent paper 12 is changed. Similarly, the second reagent paper 14 is pulled again by the motor 25 control of one of the spindles 20, 24, wound on a spindle 24 after testing is done and is stored until the entire roll 82 is changed.

With reference to FIG. 7, a contaminant sensor system, generally designated by the numeral 301 is depicted. The system 301 includes a reaction chamber 10", a reagent sheet 312, an outer housing 316, a controllable loader 318, a controllable collector 322, at least one motor 325, a controller 326, a heat source 329, and a photometer assembly 330. The reaction chamber 10", the reagent sheet or belt 312, the outer housing 316, the controllable loader 318, the controllable collector 322, the motor 325, the controller 326, the power source 328, and the photometer assembly 330 are substantially similar to the counterparts in the systems described above, except as specifically noted and/or shown, or as would be inherent.

The system 301 includes the reaction chamber 10" as discussed above, and in particular only a single a reagent sheet 312, controllable loader 318, and controllable collector 322. The reagent sheet 312 may have either a polymer 366 to dissolve a set of reagents 365 or will have those reagents 365 embedded in the sheet material itself as described above. This system 301 may be utilized for reactions that create at least one contaminant or contaminant byproduct(s) that will cause a photometric change in the sheet 312. In this system 301, the photometric system 330 is situated downward, such that the reagent sheet 312 can align with the photometer sensor 384 (not shown in FIG. 7).

System 301 includes a heat source 329 illustrated on the outer surface 336 of the reaction chamber 10", therein heating the entire reaction chamber 10" and its contents. The heat source 329 may be located on the inside of the reaction chamber 10" for a more localized heating. The heat source 329 is utilized during the reaction process of the first set of reagents 365 with a contaminant and may aid in the production of a substance contaminant(s) or contaminant byproduct(s). It is foreseen that a shaking assembly may be further included in the system 1, to aid in the speed of the reaction of reagents and contaminant(s) by oscillating the reaction chamber 10".

FIG. 8 illustrates some steps 400 that may be employed by the various systems described herein to test for a contaminant in a fluid. In step 401, a fluid sample is introduced into the reaction chamber 10". A valve 355 may control the exact amount of fluid to enter the reaction chamber 10", therein maintaining consistency in results. In step 403, a reagent sheet 312 is introduced to the fluid sample by a controllable loader 318 or a controllable collector 322. Step 403 may be such that the controller controls at least one motor 325 that operates both the controllable loader 318 and the controllable collector 322. This step may occur upon sensing that fluid (i.e. from a fluid sensor) has entered the reaction chamber 10" at a time after, or before.

At step 405, a set of reagents on the reagent sheet 312 react with the fluid sample to create a contaminant or contaminant byproduct substance(s) and capture that substance(s) on the reagent sheet 312. At step 407, a plug 362 is opened at the bottom of the reaction chamber 10" releasing the fluid and orienting the contaminant or contaminant byproduct substance(s) on the reagent sheet 312. At step 409, the reagent sheet 312 is moved to be in alignment with a photometric sensor. This step is performed by at least one of a controllable loader 318 or a controllable collector 322. At step 411, the photometric effect either of the solid or of the reagent sheet 312 is quantified and correlated to a result, i.e. contaminant concentration or level in the fluid sample. At step 413, the result is stored in memory. At step 415, the first reagent sheet 312 and solid waste is moved to the controllable collector 322. The controllable loader 318 and the controllable collector 322 may each be a spindle that rotates to roll the reagent sheet 312 about the respective spindle 318, 322.

An example of this method 400 is as follows. The method 400 for detecting a contaminant metal, chromium (VI) is initiated after water is first detected entering a solenoid valve 355 that is connected to the system 301. This detection occurs with a shorting analog water sensor 358. The valve 355 opens when water is introduced and closes after a fixed volume of the water sample (not shown) has passed through the valve 355. The water sample moves from the valve 355 to the reaction chamber 10" through a check valve (not shown), which allows the water to enter the chamber and then reseals the valve opening (not shown).

A controller 326 controls at least one motor 325 that are connected with either a controllable spindle 318 that loads or a controllable spindle 322 that collect a reagent paper or strip 312. The controller 326, such as an Arduino Pro microcontroller controls the motor 325 to rotate a spindle 318, 322 to move the first reagent paper 312 into the reaction chamber 10".

The reagent paper 312 includes a set of reagents, in this case, diphenylcarbazide. The first set of reagents, diphenylcarbazide may be sealed onto the paper 312 using a polymer, like polyvinyl alcohol (PVA) or embedded into the paper 312, for example as a nanofiber. Diphenylcarbazide is sealed within the polymer and released when the water sample comes in contact with the strip 312 thereby initiating the reaction (a) below. If there is chromium (VI) present in the water sample, (either, for example, as exists as chromate ($CrO_4^{2-}$), dichromate ($Cr_2O_7^{2-}$), hydrogen chromate ($HCrO_4^-$), hydrogen dichromate ($HCr_2O_7^-$), trichromate ($Cr_3O_{10}^{2-}$) and tetrachromate ($Cr_4O_{13}^{2-}$)), the overall chemical reaction within the reaction chamber 10" is:

a. Formation of Chromium complex

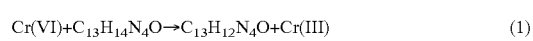

$$Cr(VI)+C_{13}H_{14}N_4O \rightarrow C_{13}H_{12}N_4O+Cr(III) \qquad (1)$$

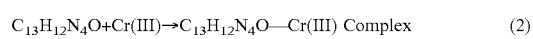

$$C_{13}H_{12}N_4O+Cr(III) \rightarrow C_{13}H_{12}N_4O\text{—}Cr(III) \text{ Complex} \qquad (2)$$

After the water sample is tested, the reaction chamber 10" is flushed by a bottom aperture (not shown) opening and the water is ejected from the reaction chamber 10". The reagent paper 312 is pulled forward at timed increments for a new sample to be tested and to be aligned with a photometric assembly 330. Chromium(VI) reacts with diphenylcarbazide to make diphenylcarbazone and chromium (III) compound. The diphenylcarbazone and chromium (III) form a $C_{13}H_{12}N_4O$—Cr(III) complex of a magenta color. The red, green and blue reflectance values of the colored spot are detected by the photometer sensor 384 (not shown) and the data is recorded in memory (not shown) by the controller 326. This color change is calibrated from a voltage to chromium (VI) concentration and this data is transmitted to computer or smart device (not shown) by the controller 326.

The solid waste (i.e. chromium complex), which remains on and adheres to the reagent paper 312, is pulled through the photometric assembly 330 by the motor 25 control of one of the spindles 318, 322, and is wound outside of the chamber 10" on a spindle 322, such that the solid waste is collected on roll 374. The solid waste and the reagent paper 312 are stored in a roll 374 until the entire roll of reagent paper 312 is changed.

With reference to FIG. 9, a contaminant sensor system, generally designated by the numeral 501 is depicted. The system 501 includes a reaction chamber 10', a first reagent sheet or belt 512, a second reagent sheet or belt 514, an outer housing 516, a first controllable loader 518, a second controllable loader 520, a first controllable collector 522, a second controllable collector 524, at least one motor 525, a controller 526, a first photometer assembly 530, and a second photometer assembly 531. The reaction chamber 10', the first reagent sheet or belt 512, the second reagent sheet or belt 514, the outer housing 516, the first controllable loader 518, the second controllable loader 520, the first controllable collector 522, the second controllable collector 524, the controller, and the first photometer assembly 530 are substantially similar to the counterparts in the systems described above, except as specifically noted and/or shown, or as would be inherent.

The system 501 includes the reaction chamber 10' as discussed above, and in particular also include a second photometer assembly 531. It is understood that the reaction chamber 10 could also be used in lieu of the reaction chamber 10'. The second photometer assembly being substantially similar to the first photometer assembly with the exception of its orientation. The second photometer assembly 531 is pointed downward. The system 501 may be utilized for reactions that create a gas, as well as, those reactions that only create a substance contaminant(s) or contaminant byproduct(s) that will cause a photometric change in the sheet 512. In this system 501, the first photometric assembly 530 is situated upward, so such that the second reagent sheet 514 can align with the photometer assembly 530 and the second photometric assembly 531 is situated downward to align with the first reagent sheet 512.

Figure 10:
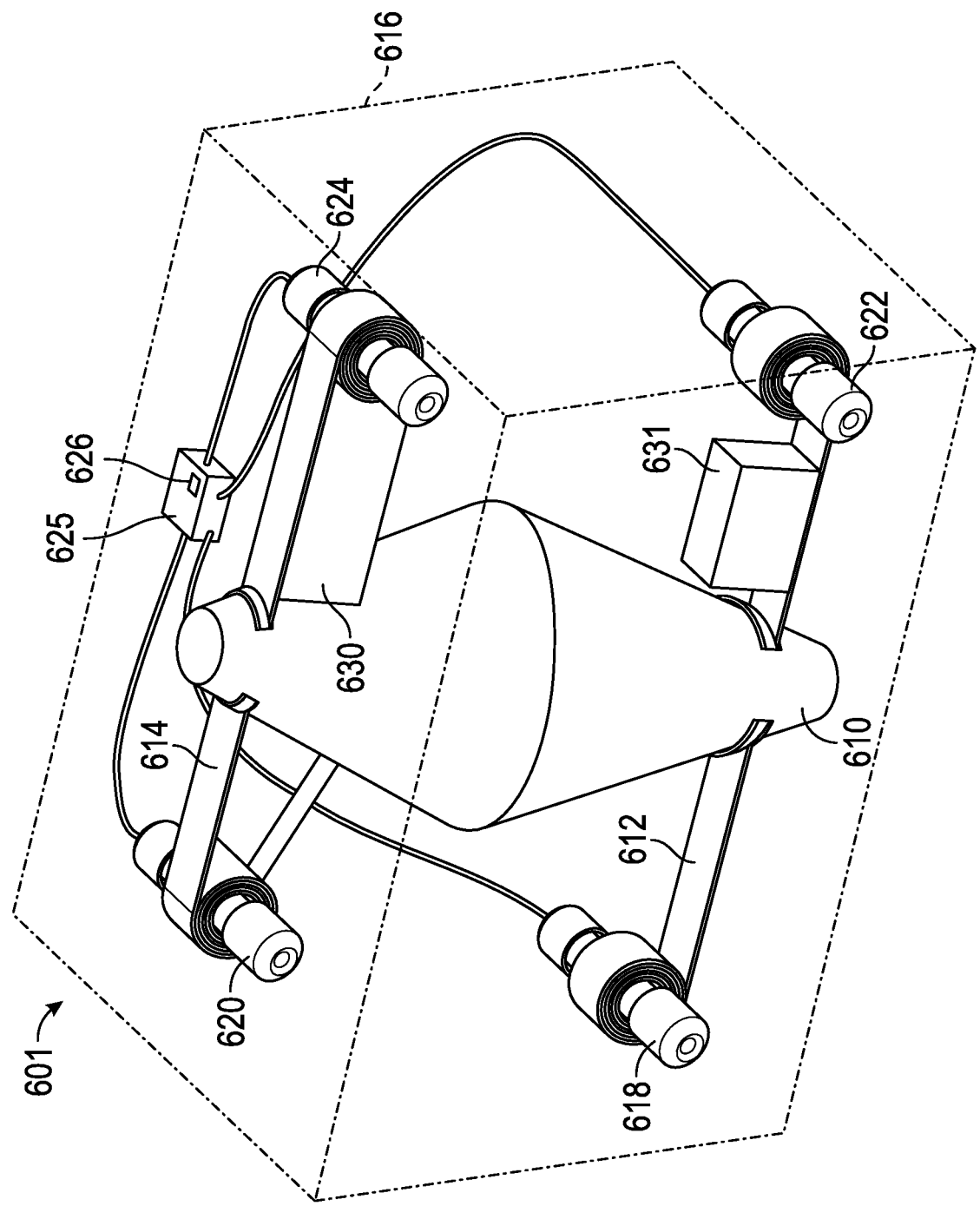
FIG. 10 is a perspective view of a contaminant sensor system according to fourth embodiment with the housing shown in phantom.

With reference to FIG. 10, a contaminant sensor system, generally designated by the numeral 601 is depicted. The system 601 includes the reaction chamber 610, a first reagent sheet or belt 612, a second reagent sheet or belt 614, an outer housing 616, a first controllable loader 618, a second controllable loader 620, a first controllable collector 622, a second controllable collector 624, at least one motor 625, a controller 626, a first photometer assembly 630 and a second photometer assembly 631. The reaction chamber 610, the first reagent sheet or belt 612, the second reagent sheet or belt 614, the outer housing 616, the first controllable loader 618, the second controllable loader 620, the first controllable collector 622, the second controllable collector 624, the controller 626, the first photometer assembly 630 and the second photometer assembly 631 are substantially similar to the counterparts in the systems described above, except as specifically noted and/or shown, or as would be inherent. In particular, the system 601 includes the reaction chamber 610, which is substantially similar to reaction chamber 10''' as discussed above (FIG. 3D), with the exception being that the second reagent sheet 614 passes through the reaction chamber 610 instead of sealing off a top thereof.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. Further, it will be understood that certain features and subcombinations may be of utility and may be employed within the scope of the disclosure. Further, various steps set forth herein may be carried out in orders that differ from those set forth herein without departing from the scope of the present methods. This description shall not be restricted to the above embodiments.

It is to be understood that while certain forms of the present invention have been illustrated and described herein, it is not to be limited to the specific forms or arrangement of parts described and shown.

The invention claimed is:

1. A contaminant sensor system comprising:
   a reaction chamber having a cavity;
   a valve connected to the reaction chamber, the valve allowing a fluid into the reaction chamber cavity;
   a first reagent sheet having a length such that the first reagent sheet enters the cavity of the reaction chamber at a first aperture and passes through the cavity of the reaction chamber at a second aperture, the first reagent sheet including at least one first reagent on the first reagent sheet, wherein the at least one first reagent reacts with the fluid in the reaction chamber;
   a first controllable loader loading an unused portion of the first reagent sheet into the reaction chamber;
   a first controllable collector collecting a used portion of the first reagent sheet;
   a first photometric detector capable of detecting a photometric property; and
   a second reagent sheet having at least one second reagent capable of changing the detectable photometric property when reacting with at least one of a contaminant and a contaminant byproduct, the at least one second reagent being embedded into the second reagent sheet and the second reagent sheet being located above the first and second apertures.

2. The contaminant sensor system of claim 1, wherein the at least one first reagent is sealed onto the first reagent sheet by a polymer, wherein the polymer releases the at least one first reagent in the fluid.

3. The contaminant sensor system of claim 2, wherein the polymer is at least one of the following: a single polymer, a co-polymer, and a composite.

4. The contaminant sensor system of claim 1, wherein the reaction chamber further comprises a third aperture located at a top of the reaction chamber, that is covered by the second reagent sheet.

5. The contaminant sensor system of claim 1, further comprising:
   a second controllable loader loading an unused portion of the second reagent sheet into the reaction chamber;
   a second controllable collector collecting a used portion of the second reagent sheet.

6. The contaminant sensor system of claim 5,
   wherein the first and second controllable loaders are first and third spindles, respectively;
   wherein the first and second controllable collectors are second and fourth spindles, respectively; and
   wherein each first and second reagent sheets are wound in a respective unused roll and extended to connect with the second and fourth spindle, respectively, to be rewound in a respective used roll.

7. The contaminant sensor system of claim 5, further comprising a controller, wherein the controller communicates with at least one motor to control at least two of the first controllable loader, the second controllable loader, the first controllable collector, and the second controllable collector.

8. The contaminant sensor of claim 7, further comprising a fluid sensor in communication with the controller.

9. The contaminant sensor system of claim 1, wherein at least one of the first and second reagent sheets may be made from at least one of the following: paper, plastic, metal, at least one natural polymer, at least one synthetic polymer, electrospun nanofiber and glass.

10. The contaminant sensor system of claim 1, wherein the second reagent sheet has a length such that the second reagent sheet enters the cavity of the reaction chamber at a third aperture and passes through the cavity of the reaction chamber at a fourth aperture.

11. The contaminant sensor system of claim 10, wherein a portion of the first reagent sheet is sealed within the cavity of the reaction sheet, and wherein the reaction chamber further includes at least one controllable door capable of opening and closing at least one of the first, second, third, and fourth apertures.

12. The contaminant sensor system of claim 1, further comprising a controller, the controller communicating with the photometric detector and a database to store results from the photometric detector.

13. The contaminant sensor system of claim 12, wherein the controller includes a transceiver.

14. The contaminant sensor of claim 12, wherein the database is in communication with at least two contaminant sensor systems.

15. The contaminant sensor of claim 1, wherein the valve allows a predetermined amount of fluid into the reaction chamber.

16. The contaminant sensor system of claim 1, wherein the first reagent sheet is capable of changing the detectable photometric property when reacting with at least one of a contaminant and a contaminant byproduct.

17. The contaminant sensor system of claim 1, further comprising a second photometric detector, wherein the first and second photometric detectors are aligned to the respective used portions of the first and second reagent sheets.

* * * * *